(12) United States Patent
Suh et al.

(10) Patent No.: US 7,666,631 B2
(45) Date of Patent: Feb. 23, 2010

(54) **ADENOSYLMETHIONINE SYNTHETASE FROM *STREPTOMYCES SP.*, GENE SEQUENCES CODING THE SAME AND METHOD FOR MASS PRODUCTION OF SECONDARY METABOLITES INCLUDING ANTIBIOTICS THEREOF**

(75) Inventors: Joo-Won Suh, 8-ho, Myungjimaeul, San 33-1, Nam-dong, Yongin-city 449-728, Kyonggi-do (KR); Young-Yell Yang, Pohang (KR); In-Hyung Lee, Seoul (KR); Dong-Jin Kim, Ockcheon-gun (KR); Chang-Gu Hyun, Yongin (KR)

(73) Assignee: Joo-Won Suh, Yongin (KR)

( * ) Notice: Subject to any disclaimer, the term of this patent is extended or adjusted under 35 U.S.C. 154(b) by 0 days.

(21) Appl. No.: 10/491,492

(22) PCT Filed: Jul. 16, 2002

(86) PCT No.: PCT/KR02/01344

§ 371 (c)(1),
(2), (4) Date: Apr. 1, 2004

(87) PCT Pub. No.: WO03/008591

PCT Pub. Date: Jan. 30, 2003

(65) Prior Publication Data

US 2005/0112728 A1    May 26, 2005

(30) Foreign Application Priority Data

Jul. 16, 2001    (KR) ............................ 2001-0042931

(51) Int. Cl.
*C12P 21/04* (2006.01)
*C12N 9/10* (2006.01)
*C12P 21/06* (2006.01)
*C12N 15/00* (2006.01)
*C12N 1/20* (2006.01)

(52) U.S. Cl. ..................... 435/71.3; 435/193; 435/69.1; 435/320.1; 435/252.3; 435/252.35; 435/253.5

(58) Field of Classification Search ....................... None
See application file for complete search history.

(56) References Cited

U.S. PATENT DOCUMENTS 5,712,146 A * 1/1998 Khosla et al. ................. 506/14
6,312,920 B1 * 11/2001 DeHoff et al. ............. 435/69.1

FOREIGN PATENT DOCUMENTS

JP          09-224690         9/1997

OTHER PUBLICATIONS

Merali, S. et al. "Continuous axenic cultivation of *Pneumocystis carinii*", Proc.Natl.Acad.Sci. USA, vol. 96 pp. 2402-2407, 1999.

* cited by examiner

*Primary Examiner*—Ganapathirama Raghu
(74) *Attorney, Agent, or Firm*—Birch, Stewart, Kolasch & Birch, LLP (57) ABSTRACT

Disclosed is an isolated nucleotide sequence encoding an enzyme catalyzing biosynthesis of SAM (SAM-s) and its amino acid sequence. Also, the present invention provides a method for mass production of a useful secondary metabolite including antibiotics using the isolated nucleotide sequence and SAM, where SAM acts as a methyl group donor.

3 Claims, 4 Drawing Sheets

ADENOSYLMETHIONINE SYNTHETASE FROM *STREPTOMYCES SP.*, GENE SEQUENCES CODING THE SAME AND METHOD FOR MASS PRODUCTION OF SECONDARY METABOLITES INCLUDING ANTIBIOTICS THEREOF

TECHNICAL FIELD

The present invention relates to S-adenosyl-L-methionine synthetase and a nucleotide sequence encoding the same, and more particularly, to an isolated nucleotide sequence encoding an enzyme catalyzing biosynthesis of SAM (SAM-s) from adenosyl triphosphate (ATP) and methionine, and its amino acid sequence. Also, the present invention is concerned with a method for mass production of a useful secondary metabolite including antibiotics using the nucleotide sequence and SAM.

PRIOR ART

S-adenosyl-L-methionine (SAM) is well known to play a critical role in cell growth and differentiation, essential for survival of living organisms including human beings. In living cells, SAM acts as a methyl group donor as well as a precursor for an amninopropyl group in a biosynthesis pathway of polyamine, where the methyl group and the polyamine are utilized in primary and secondary metabolisms.

It has been reported that SAM positively or negatively affects growth of bacteria including *E. coli* and *Bacillus subtilis*, thus causing their life cycles to change in a manner of inhibiting cell growth or stimulating morphological differentiation.

In addition, the biological function of SAM is also found to be essential for primary and secondary metabolisms in plants and animals. Especially, it has been reported that SAM as a methyl group donor affects differentiation, causing morphological changes in plant or animal cells.

On the other hand, spectinomycin, which is an antibiotic derived from *Streptomyces spectabilis*, belongs to an aminoglycoside family and is composed of one sugar and two methyl groups originated from a methyl group donor, SAM.

DISCLOSURE OF THE INVENTION

Based on the fact that methyl groups of spectinomycin are derived from SAM, inventors of the present invention conducted intensive and thorough research into effects of SAM on biosynthesis of spectinomycin, resulting in the finding that SAM positively affects the biosynthesis of antibiotics, thereby increasing their production yield.

Therefore, it is an object of the present invention to provide an isolated nucleotide sequence encoding an enzyme catalyzing biosynthesis of SAM from *Streptomyces spectabilis* ATCC 27741 and an amino acid sequence translated from the isolated nucleotide sequence.

It is another object of the present invention to provide a method of increasing production of a useful secondary metabolite including antibiotics using SAM.

In accordance with the present invention, the first object is achieved by isolating a gene encoding an enzyme catalyzing SAM biosynthesis, which is derived from *S. spectabilis*, by obtaining a PCR product of 4.0 kb from a gene library of *S. spectabilis* using PCR, and confirming presence of a gene of about 1.2 kb in the PCR product encoding an enzyme catalyzing SAM biosynthesis, by sequencing the PCR product assaying activity of its translational product.

In accordance with the present invention, the second object is achieved by producing SAM, which is synthesized by the translational product of the isolated nucleotide sequence or that which is commercially available, having an ability to stimulate production of an antibiotic.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

In accordance with the present invention, there is provided an enzyme catalyzing biosynthesis of S-adenosyl-L-methionine having an amino acid sequence consisting of the sequence shown in SEQ ID NO. 2, which is derived from *Streptomyces spectabilis* ATCC 27741.

In accordance with the present invention, there is provided an isolated nucleotide sequence consisting of the sequence shown in SEQ ID NO. 1, which encodes the amino acid sequence of SEQ ID NO. 2.

In accordance with the present invention, there is also provided a method of producing a useful secondary metabolite including antibiotics in a *Streptomyces* species-originated transformant into which a gene encoding an enzyme catalyzing biosynthesis of SAM is introduced, thereby improving productivity of the useful secondary metabolite.

In accordance with the present invention, there is further provided a method of producing a useful secondary metabolite including antibiotics by directly adding SAM to culture medium containing antibiotic-producing bacteria, thereby improving productivity of the useful secondary metabolite.

In the present invention, preferable examples of the useful secondary metabolite include antibiotics, such as polyketide antibiotics, anti-cancer agents, and vermicides.

In the present invention, a gene encoding an enzyme catalyzing SAM biosynthesis (SAM-s) is isolated from cosmid clones containing genes encoding enzymes stimulating biosynthesis of spectinomycin, which is obtained from a cDNA library of *S. spectabilis* ATCC 27741, where a 3.9 kb clone is primarily obtained. The nucleotide sequence of the 3.9 kb clone is partially determined by performing nucleotide sequencing, and its homology to known SAM synthetases, which mediate biosynthesis of SAM using ATP and methionine as substrates, is examined, based on the obtained nucleotide sequence, indicating the possible presence of a gene encoding an enzyme catalyzing SAM biosynthesis. The 3.9 kb clone is demonstrated to carry the gene encoding the enzyme catalyzing SAM biosynthesis by in vitro assaying the activity of its translated product.

In accordance with the present invention, a portion of the 3.9 kb clone, containing the gene encoding an enzyme catalyzing SAM biosynthesis (SAM-s), is introduced into *Streptomyces* species to assay production yield of an antibiotic, actinorhodin, and also, the effect of SAM on production of antibiotics is further investigated through direct treatment of cells with SAM, thereby demonstrating that SAM is effective in improving productivity of secondary metabolites including antibiotics.

In embodiments of the present invention, *Streptomyces lividans* TK23, which is commercially available, is transformed with the gene encoding "SAM-s", and the resulting transformant exhibits mass production of actinorhodin, demonstrating that SAM is effective in enhancing antibiotic productivity of cells. Herein, application of SAM for high production of antibiotics is not limited to the transformant and the antibiotic, actinorhodin, but the effectiveness of SAM on production of antibiotics can be achieved with all *Streptomyces* species transformed with a gene encoding an enzyme catalyzing SAM biosynthesis.

In addition, when SAM is directly added to culture medium containing antibiotic-producing bacteria, productivity of antibiotics is increased 5 to 10 times, and especially, production of polyketide antibiotics is significantly increased.

The present invention will be explained in more detail with reference to the following examples in conjunction with the accompanying drawings. However, the following examples are provided only to illustrate the present invention, and the present invention is not limited to them.

EXAMPLE 1

Cloning of a Gene Encoding an Enzyme Capable of SAM Biosynthesis from Cosmid Clones of *Streptomyces spectabilis* ATCC 27741

Genes encoding enzymes catalyzing biosynthesis of an antibiotic are typically located together in a specific region of a genome. Therefore, there was used two cosmid clones harboring 30 to 40 kb fragment, which carries a gene family consisting of genes encoding enzymes participating in spectinomycin biosynthesis and may also include a gene encoding methyltransferase enzyme, one of enzymes mediating spectinomycin biosynthesis, which functions to transfer methyl groups. After digestion of the two cosmid clones with restriction enzymes, Southern Blotting was performed using metK gene, having high homology to methlytransferase at the nucleotide sequence level, as a probe.

As a result of Southern Blotting, a positive spot was observed, indicating a 3.9 kb fragment inserted into a BamHI site of pHCG121. 3.9 kb fragment was then subcloned into a BamHI site of pBluescript KS(+), giving a recombinant plasmid pHCG1647. From the subcloned 3.9 kb fragment, a 2.5 kb fragment, which is believed to carry a gene encoding an enzyme catalyzing SAM biosynthesis, was subcloned again into pBluescript KS(+) to form a recombinant plasmid pJWK0012.

EXAMPLE 2

Figure 1:
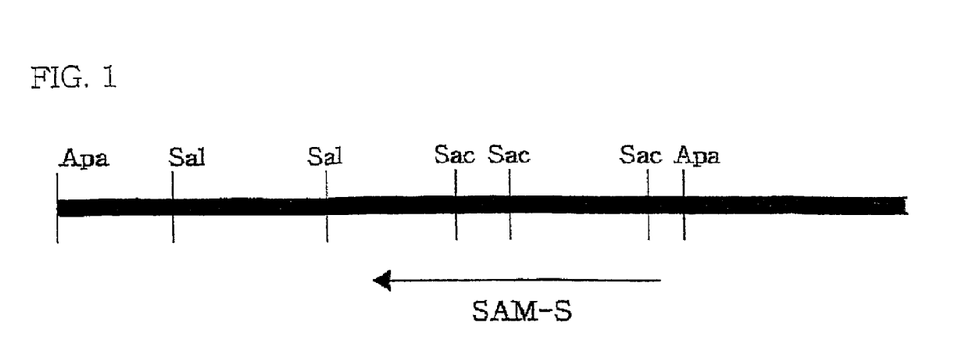
FIG. 1 is a restriction map of a gene encoding an enzyme catalyzing SAM biosynthesis (SAM-s) carried in a recombinant plasmid, pJWK0012, which is originated from an *E. coli* plasmid.

Determination of Nucleotide Sequence of the Cloned 2.5 kb Fragment and its Corresponding Amino Acid Sequence In order to determine a nucleotide sequence of the cloned 2.5 kb fragment and its corresponding amino acid sequence, the 2.5 kb insert carried in pJWK0012 prepared in the Example 1 was digested with restriction enzymes, ApaI, SalI and SacI, and then subcloned, followed by nucleotide sequencing. FIG. 1 shows a restriction map of the 2.5 kb fragment in pJWK0012 and its translational orientation.

Based on the nucleotide sequence of the 2.5 kb fragment, its amino acid sequence was obtained through search using a Codon Preference program (Bibb, M. J. et al., Gene, 1984). As a result, the 2.5 kb fragment was found to have an open reading frame consisting of a coding region ranging from nt 835 to nt 2051, which may express a protein consisting of 464 amino acid. The translational product of the open reading frame was, in the present invention, called "SAM-s".

To investigate the homology of "SAM-s" to other known proteins, the amino acid sequence of "SAM-s" was compared to those of SAM synthetases of *Streptomyces coelicolor*, *Bactillus subtilis* and *Escherichia coli*, which were obtained from GeneBank DataBase (USA). It was found that "SAM-s" shares high homology with other synthetases. Also "SAM-s" of the present invention was found to have homology to some methyltransferases from microorganisms.

EXAMPLE 3

Assay for Activity of "SAM-s"

In order to analyze activity of "SAM-s", the gene encoding "SAM-s" was expressed in *E. coli*, and the resulting translational product, "SAM-s", was then isolated.

To express the gene encoding "SAM-s" in *E. coli*, the gene was inserted into a pET-21a vector, and then introduced into *E. coli* BL21. The expressed gene product, "SAM-s" was isolated using a His-Tag purification system. Thereafter, 10 to 50 µl of the enzyme solution containing the protein "SAM-s" was added to a reaction mixture containing 100 mM of Tris-HCl, 200 mM of KCl, 10 mM of $MgCl_2$, 1 mM DTT, 5 mM ATP, and 5 mM methionine, followed by incubation for 120 min at 30° C. After the incubation, reaction products were analyzed through HPLC using Reverse C18 column. In this regard, the column loaded with sample was initially equilibrated with a solution of 0.1 M of $NaH_2PO_4$/acetonitrile at a ratio of 98:2 (V/V), pH 2.65. Then, a second solution comprising 0.15 M $NaH_2PO_4$/acetonitrile at a ratio of 74:26 (V/V) was applied with continuous mixing with the first solution, forming a concentration gradient.

Figure 2:
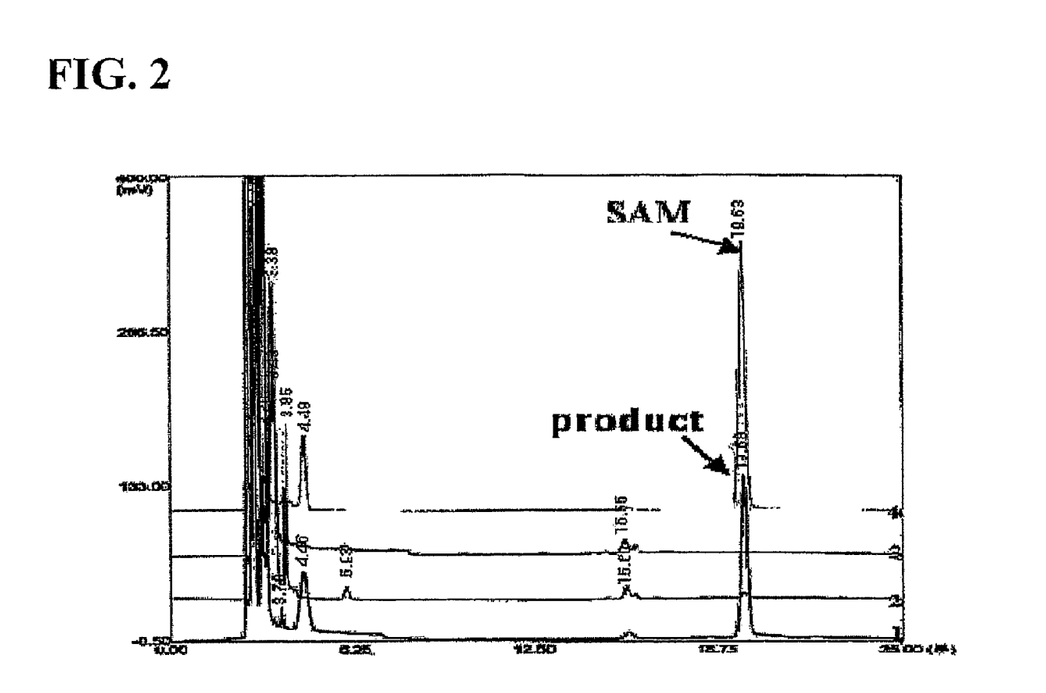
FIG. 2 is a graph showing an ability of "SAM-s" to synthesize SAM, using BPLC, where commercially available SAM is used as a control.

As shown in FIG. 2, the product of the catalytic activity of the protein expressed in *E. coli* is proven to be SAM. That is, when the expressed protein is supplied with ATP and methionine as substrates, the product has an HPLC retention time identical to commercially available SAM, indicating that the protein expressed in *E. coli* has an activity to synthesize SAM using ATP and methionine as substrates.

The gene encoding "SAM-s" was first inserted into pWHM3, which is a shuttle vector between *E. coli* and *Streptomyces* species, giving an expression vector pSAM-s. The plasmid pSAM-s was then introduced into *S. lividans* TK23. The resulting transformant, *Streptomyces lividans* TK-23 harboring pSAM-s, was deposited in the Korean Culture Center of Microorganisms with accession No. KCCM 10397 on Jul. 2, 2002. The transformant was incubated in one liter of a medium including 50 g of glycerol, 5 g of glutamic acid, 21 g of morpholinopropane sulfonic acid, 200 mg of $MgSO_4 7H_2O$, 100 mg of $CaCl_2 2H_2O$, 100 mg NaCl, 82 mg $KH_2PO_4$, 9 mg $FeSO_4 7H_2O$, and 2 ml of trace element solution, adjusted to pH 6.5. During incubation for 7 days at 28°

Figure 4:
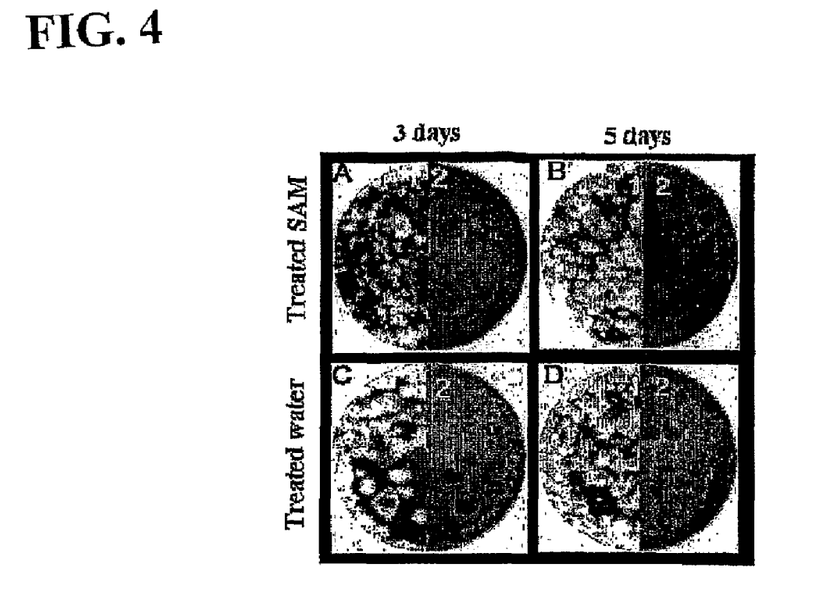
FIG. 4 is a photograph showing an effect of SAM produced by "SAM-s" on production yield of actinorhodin in *S. lividans* TK23 treated with commercially available SAM.

C., production yield of actinorhodin, which is a main antibiotic produced from *S. lividans* TK23, was analyzed. The results are shown in FIG. 4.

Figure 3:
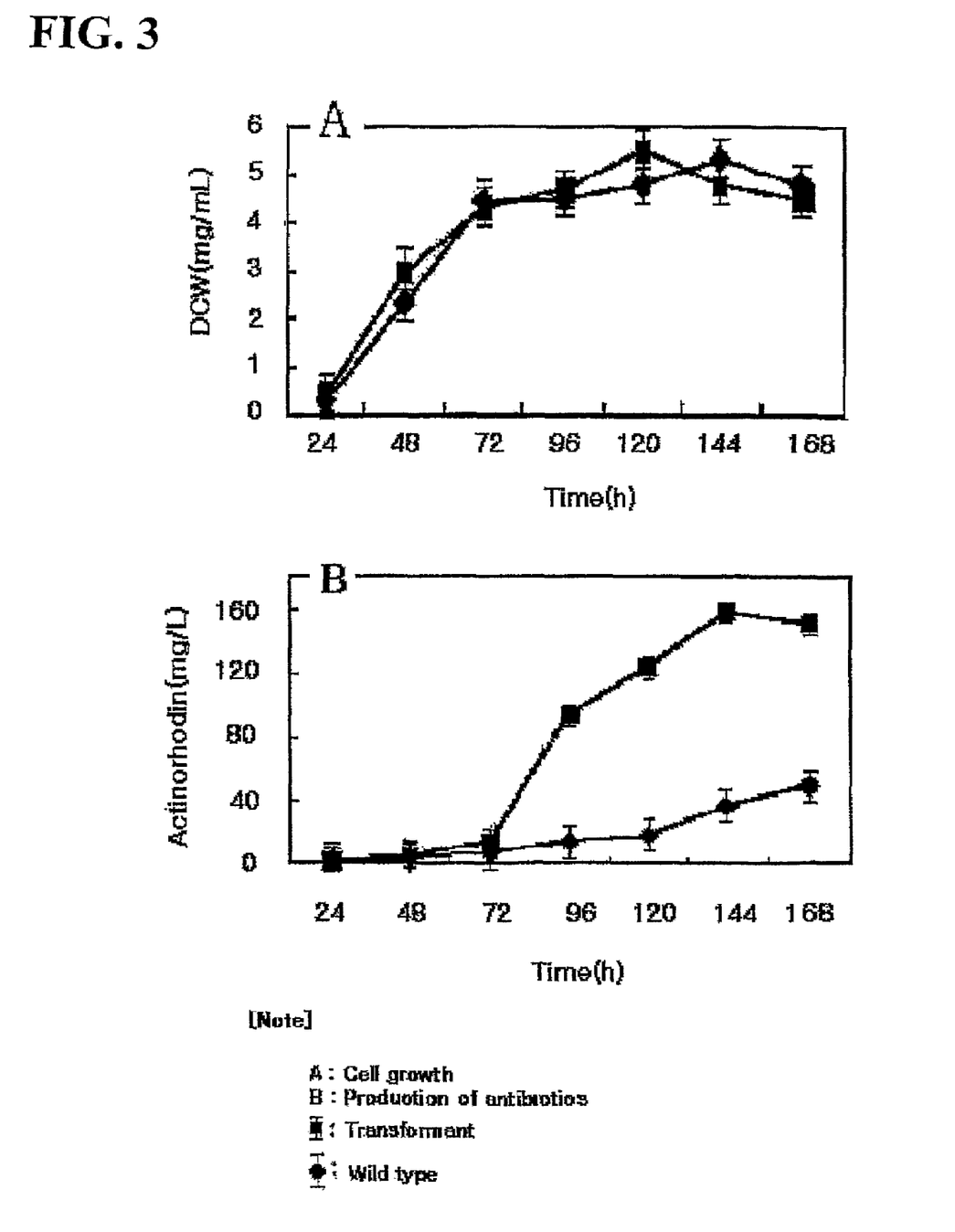
FIG. 3 is a graph showing an effect of SAM produced by "SAM-s" on production yield of actinorhodin in *S. lividans* TK23 transformed with a gene encoding "SAM-s"

As apparent in FIG. 3, when SAM was over-produced in *S. lividans* TK 23 through over-expression of "SAM-s", it was observed that production of actinorhodin in the transformant was enhanced to over six times in comparison with that of a wild type *S. lividans*.

EXAMPLE 5

Effect of Externally Added SAM on Productivity of Actinorhodin

Based on the finding that in vivo over-expressed SAM positively affects production yield of actinorhodin in *S. lividans* TK23, an effect of SAM on productivity of actinorhodin was investigated when commercially available SAM is added directly to culture medium containing *S. lividans* TK23. As such, wild type *S. lividans* TK23 was treated with 1 mM of commercially available SAM.

The result is shown in FIG. 4, where actinorhodin produced in *S. lividans* TK23 treated with SAM, and the control not treated with SAM, indicated by a blue color. As shown in FIG. 4, it was found that *S. lividans TK*23 treated with SAM produces more actinorhodin than *S. lividans* TK23 not treated with SAM, demonstrating that SAM positively affects productivity of actinorhodin.

EXAMPLE 6

Effect of SAM on Productivity of Undecylprodigiosin in *S. lividans* TK23

*S. lividans* TK23 transformed with the vector pSAM-s was incubated under the same culture conditions as those used for production of actinorhodin. To determine the amount of undecylprodigiosin produced, after adjusting pH to 12, absorbance was measured at 468 nm, and concentration of the antibiotic was calculated according to the following formula: concentration=OD value×9.4673.

Figure 5:
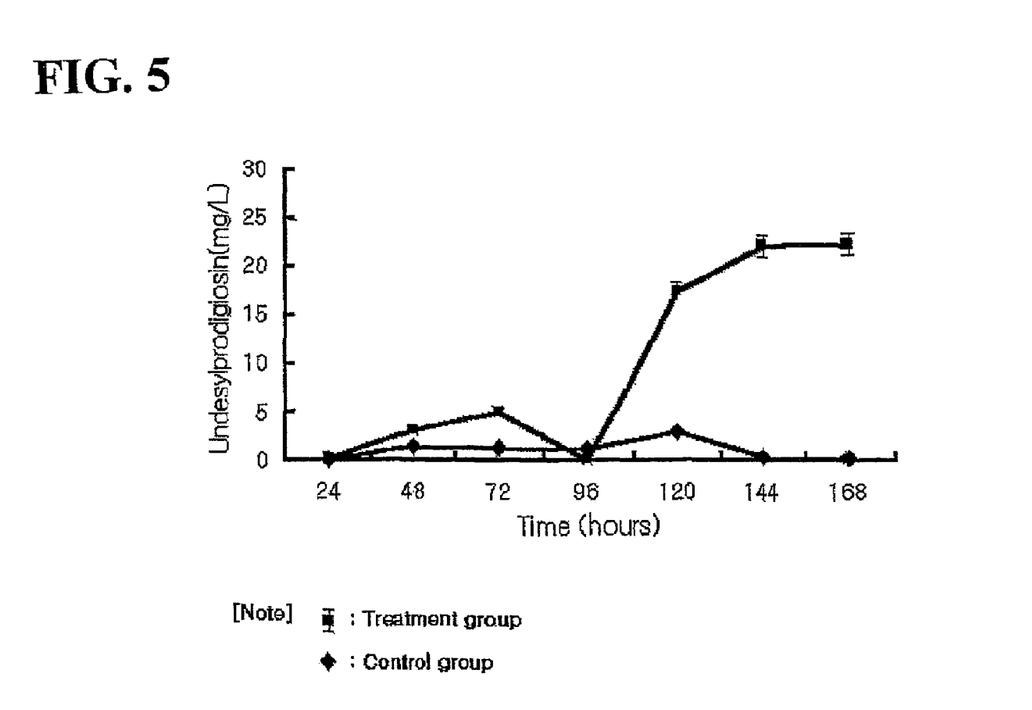
FIG. 5 is a graph showing an effect of SAM on production yield of undecylprodigiosin in *S. lividans* TK23.

As apparent FIG. 5, productivity of undecylprodigiosin was very high in comparison with a control not transformed with the vector pSAM-s, indicating that SAM positively affects production yield of undecylprodigiosin.

EXAMPLES 7 to 13

Effect of SAM on Productivity of Antibiotics in *Streptomyces* species

TABLE 1

| | | Culture medium and culture condition | |
|---|---|---|---|
| Exp. | Antibiotic | *Streptomyces* sp. | Culture medium (/L) and culture condition |
| 7 | Avermectin | *S. avermitilis* | 15 g glucose, 0.5 g asparagine, 0.5 g $K_2HPO_4$, pH 7.0, 25° C., incubation for 5 days |
| 8 | Monensin | *S. cinnamonensis* | 2.5% glucose, 1.5% soybean meal, 0.3% $CaCO_3$, 0.03% $FeSO_4 7H_2O$, 0.003% $MnCl_2 4H_2O$, pH 7.0, 30° C., incubation for 5 days |
| 9 | Spectinomycin | *S. spectabilis* | 10 g Maltose, 5 g tryptone, 1 g $K_2HPO_4$, 2 g NaCl, pH7.0, 30° C., incubation for 5 days |
| 10 | Doxorubicin | *S. peucetius* | 60 g Glucose, 8 g yeast extract, 20 g malt extract, 2 g NaCl, 15 g MOPS sodium salt, 0.1 g $MgSO_4$, 0.01 g $FeSO_4 7H_2O$, 0.01 g $ZnSO_4 7H_2O$, pH 7.0, 30° C., incubation for 5 days |
| 11 | Streptomycin | *S. griseus* | 1% glucose, 0.4% peptone, 0.2% meat extract, 0.2% yeast extract, 0.5% NaCl, 0.025% $MgSO_4 7H_2O$, pH 7, 30° C., incubation for 5 days |
| 12 | Tetracyclin | *S. aureofaciens* | 3% corn flour, 4% corn steep liquor, 5% corn starch, 0.7% $(NH_4)_2SO_4$, 0.1% $NH_4Cl$, 5 ppm $CoCl_2$, 0.9% $CoSO_3$, 2% rice bran oil, pH7, 28° C., incubation for 5 days |
| 13 | Chlortetracyclin | *S. aureofaciens* | 1% sucrose, 1% corn steep liquor, 0.2% $(NH_4)_2HPO_4$, 0.2% $KH_2PO_4$, 0.1% $CaCO_3$, 0.025% $MgSO_4 7H_2O$, 0.005% $ZnSO_4 7H_2O$, 0.00033% $CuSO_4 5H_2O$, 0.00033% $MnCl_2 4H_2O$, incubation for 5 days |

Each *Streptomyces* species was incubated in its corresponding culture medium according to Table 1, and treated with 1 mM of SAM (Sigma, USA). After incubation for 5 days, antibiotic concentration was measured in each culture medium. The results are given in Table 2, below. It was found that each *Streptomyces* species, as a treatment group, produces a much higher amount of its specific antibiotic than a control group not treated with SAM.

TABLE 2

Production amount of an antibiotic in *Streptomyces* sp. treated or not treated with SAM

| Exp. | Antibiotic | *Streptomyces* sp. | Production amount of a control group (µg/ml) | Production amount of a treatment group (µg/ml) |
|---|---|---|---|---|
| 7 | Avermectin | *S. avermitilis* | 5 | 25 |
| 8 | Monensin | *S. cinnamonensis* | 30 | 180 |
| 9 | Spectinomycin | *S. spectabilis* | 5 | 35 |
| 10 | Doxorubicin | *S. peucetius* | 38 | 300 |
| 11 | Streptomycin | *S. griseus* | 101 | 602 |
| 12 | Tetracycline | *S. aureofaciens* | 30 | 188 |
| 13 | Chlortetracycline | *S. aureofaciens* | 25 | 130 |

As shown in Table 2, *Streptomyces* species treated with SAM produced 5 to 10 times more antibiotic than the control, indicating that SAM positively affects production yield of various antibiotics.

INDUSTRIAL APPLICABILITY

As described hereinbefore, the present invention provides an isolated nucleotide sequence of a gene encoding an enzyme catalyzing biosynthesis of SAM, which is derived from *Streptomyces spectabilis* ATCC 27741, and its amino acid sequence. SAM, which is produced by the enzyme of the present invention or purchased commercially, is very effective in increasing productivity of various antibiotics. Therefore, the isolated nucleotide sequence of the present invention is capable of being utilized in mass production of secondary metabolites including antibiotics, and thus is very useful in pharmaceutical industries.

The invention claimed is:

1. A method for production of an antibiotic comprising the steps:
   i) producing S-adenosyl-L-methionine by transforming a *Streptomyces* species selected from the group consisting of *Streptomyces spectabilis, Streptomyces lividans, Streptomyces avermitilis, Streptomyces cinnamonenesis, Streptomyces peucetius, Streptomyces griseus*, and *Streptomyces aureofaciens* with an expression vector comprising a polynucleotide obtained from *Streptomyces spectabilis* ATCC 27741 encoding a polypeptide having the enzymatic activity of catalyzing the biosynthesis of said S-adenosyl-L-methionine, wherein said polypeptide has the amino acid sequence of SEQ ID NO: 2; and
   ii) culturing said transformed *Streptomyces* species producing said S-adenosyl-L-methionine in an antibiotic culture medium for the mass production of antibiotics, wherein said antibiotics are avermectin, monensin, spectinomycin, doxorubicin, streptomycin, tetracycline, chlortetracycline, actinorhodin or undecylprodigiosin.

2. The method for mass production of claim 1, wherein the *Streptomyces lividians* is *Streptomyces lividians* TK23.

3. The method for mass production of claim 2, wherein the *Streptomyces lividians* TK23 has an accession No. KCCM 10397 (Korean Culture Center of Microorganisms).

* * * * *

SEQUENCE LISTING

```
<160> NUMBER OF SEQ ID NOS: 3

<210> SEQ ID NO 1
<211> LENGTH: 2349
<212> TYPE: DNA
<213> ORGANISM: Steptomyces spectabilis ATCC 27741
<220> FEATURE:
<221> NAME/KEY: CDS
<222> LOCATION: (837)..(2096)

<400> SEQUENCE: 1
gggcccgcgt cacgctcgtc gcggcgaaca ccgcgctgcc ggacccggcg ggcgtcgacc      60
tcgtgcccgt gggcaccgcc gtacagctcc gcgaggccgt cctgaaggcg gccgccgacg     120
ccgacgcggt ggtgatggcc gccgccgtgg ccgacttccg cccggccgcg tacgccgccg     180
gaaagatcaa gaagcaggac ggcgaggacc cggcccccgct caccctcgtc cgcaatccgg     240
atatcctcgc cgagctctcg ggcgaccgcc cgcgccccgg ccaggtcgtc gtcggcttcg     300
cggccgagac ggacaacgtg ctggccaacg gcgggccaag ctcgcccgca aggctgcgac     360
ctcctcgtag tgaacgaagt cggtgagcgc aagatgttcg gctctgagcg gaacgaggcc     420
gtggtgctcg gtgccgacgg cagtgagacg ccggtgccct acggccccaa ggacgatctc     480
gccgacacgg tctgggatct ggtcgcaccg cgccttgacc ggtcgtaaca cgcctgaggc     540
catcggtccg gatcgtggcc gggccgatgg ccggaaccgg ccccggcgcg ccatgcgccc     600
ctccaggctc tctaaaccca ccctaaaccc gccaaatgcg ggccttgagc cctctggtgg     660
agaccgatcg tcgtatcgca caatgcagtg ccgcaggtca caggcctctc ttctgacgag     720
agaggtggcc atgcggccgt gtgtgaccga taaactggtc tcggacgtcg tcgagcgcag     780
ctctcggccc gtccatcaat gatcagccag cagccgctgc aaccacaggg agcgtg atg     839
                                                                     Met
                                                                      1 tcc cgc cgt ctc ttc acc tcg gag tcc gtg acc gag ggt cac ccc gac       887
Ser Arg Arg Leu Phe Thr Ser Glu Ser Val Thr Glu Gly His Pro Asp
```

-continued

|     | 5   |     |     |     | 10  |     |     |     | 15  |     |     |     |      |
|-----|-----|-----|-----|-----|-----|-----|-----|-----|-----|-----|-----|-----|------|
| aag | atc | gct | gac | cag | atc | agc | gac | acc | att | ctc | gac | gcg | ctt | ctg | cgt | 935  |
| Lys | Ile | Ala | Asp | Gln | Ile | Ser | Asp | Thr | Ile | Leu | Asp | Ala | Leu | Leu | Arg |      |
|     |     | 20  |     |     |     | 25  |     |     |     | 30  |     |     |     |     |     |      |

```
aag atc gct gac cag atc agc gac acc att ctc gac gcg ctt ctg cgt      935
Lys Ile Ala Asp Gln Ile Ser Asp Thr Ile Leu Asp Ala Leu Leu Arg
         20                  25                  30 gag gac ccg acg tcc cgg gtc gcc gtc gaa acg ctc atc acc acc ggc      983
Glu Asp Pro Thr Ser Arg Val Ala Val Glu Thr Leu Ile Thr Thr Gly
 35                  40                  45 ctc gtg cac gtc gcc ggt gag gtc acg acc aag gcg tac gcg ccg atc     1031
Leu Val His Val Ala Gly Glu Val Thr Thr Lys Ala Tyr Ala Pro Ile
 50                  55                  60                  65 gcg cag ctg gtg cgc gag aag atc ctc gag atc gga tac gac tcc tcg     1079
Ala Gln Leu Val Arg Glu Lys Ile Leu Glu Ile Gly Tyr Asp Ser Ser
             70                  75                  80 aag aag ggc ttc gac ggc gcc tcc tgc ggc gtc tcg gtg tcc atc ggc     1127
Lys Lys Gly Phe Asp Gly Ala Ser Cys Gly Val Ser Val Ser Ile Gly
                 85                  90                  95 gcg cag tcc ccg gac atc gcg cag ggc gtc gac acg gcg tac gag agc     1175
Ala Gln Ser Pro Asp Ile Ala Gln Gly Val Asp Thr Ala Tyr Glu Ser
            100                 105                 110 cgt gtc gag ggc gac gag gac gag ctc gac cgg cag ggc gcc ggt gac     1223
Arg Val Glu Gly Asp Glu Asp Glu Leu Asp Arg Gln Gly Ala Gly Asp
    115                 120                 125 cag ggc ctg atg ttc ggc tac gcc tgc gac gag acc ccg gag ctg atg     1271
Gln Gly Leu Met Phe Gly Tyr Ala Cys Asp Glu Thr Pro Glu Leu Met
130                 135                 140                 145 ccg ctc ccg atc cac ctc gcg cac cgc ctc tcg cgc cgc ctc tcc gag     1319
Pro Leu Pro Ile His Leu Ala His Arg Leu Ser Arg Arg Leu Ser Glu
                150                 155                 160 gtg cgc aag aac ggg acc atc ccc tac ctg cgc ccc gac ggc aag acc     1367
Val Arg Lys Asn Gly Thr Ile Pro Tyr Leu Arg Pro Asp Gly Lys Thr
            165                 170                 175 cag gtc acc atc gag tac gac ggc gac aag gcc gtc cgc ctc gac acg     1415
Gln Val Thr Ile Glu Tyr Asp Gly Asp Lys Ala Val Arg Leu Asp Thr
        180                 185                 190 gtc gtc gtc tcc tcg cag cac gcg tcg gac atc gac ctg gag tcg ctg     1463
Val Val Val Ser Ser Gln His Ala Ser Asp Ile Asp Leu Glu Ser Leu
    195                 200                 205 ctc gcc ccc gac atc cgc gag ttc gtc gtc gag ccg gag ctc aag gcc     1511
Leu Ala Pro Asp Ile Arg Glu Phe Val Val Glu Pro Glu Leu Lys Ala
210                 215                 220                 225 ctg gtc gag gac ggc atc aag ctg gtc gtc gag ccg gag ctc aag gcc     1559
Leu Val Glu Asp Gly Ile Lys Leu Val Val Glu Pro Glu Leu Lys Ala
                230                 235                 240 ctg gtc gag gac ggc atc aag ctg gag acc gag ggc tac cgc ctc ctg     1607
Leu Val Glu Asp Gly Ile Lys Leu Glu Thr Glu Gly Tyr Arg Leu Leu
            245                 250                 255 gtc aac ccg acc ggc cgc ttc gag atc ggc ggc ccg atg ggt gac gcg     1655
Val Asn Pro Thr Gly Arg Phe Glu Ile Gly Gly Pro Met Gly Asp Ala
        260                 265                 270 ggc ctg acc ggc cgc aag atc atc atc gac acc tac ggc ggc atg tcc     1703
Gly Leu Thr Gly Arg Lys Ile Ile Ile Asp Thr Tyr Gly Gly Met Ser
    275                 280                 285 cgc cac ggc ggc ggc gcc ttc tcc ggc aag gac ccg tcc aag gtg gac     1751
Arg His Gly Gly Gly Ala Phe Ser Gly Lys Asp Pro Ser Lys Val Asp
290                 295                 300                 305 cgc tcg gcg gcg tac gcg atg cgc tgg gtc gcc aag aac gtg gtg gcc     1799
Arg Ser Ala Ala Tyr Ala Met Arg Trp Val Ala Lys Asn Val Val Ala
                310                 315                 320 gcg ggc ctc gcc tcg cgc tgc gag gtc cag gtc gcc tac gcc atc ggc     1847
```

-continued

```
Ala Gly Leu Ala Ser Arg Cys Glu Val Gln Val Ala Tyr Ala Ile Gly
            325                 330                 335 aag gcc gag ccg gtc ggt ctg ttc gtc gag acc ttc ggc acc aac acg    1895
Lys Ala Glu Pro Val Gly Leu Phe Val Glu Thr Phe Gly Thr Asn Thr
            340                 345                 350 atc gac acg gac aag atc gag cag gcc atc agc gag gtc ttc gac ctc    1943
Ile Asp Thr Asp Lys Ile Glu Gln Ala Ile Ser Glu Val Phe Asp Leu
        355                 360                 365 cgc ccg gcc gcg atc atc cgc agc ctc gac ctg ctc cgc ccg atc tac    1991
Arg Pro Ala Ala Ile Ile Arg Ser Leu Asp Leu Leu Arg Pro Ile Tyr
370                 375                 380                 385 tcc cag acc gcc gcg tac ggc cac ttc ggc cgc tcg ctg ccg gag ttc    2039
Ser Gln Thr Ala Ala Tyr Gly His Phe Gly Arg Ser Leu Pro Glu Phe
                390                 395                 400 acc tgg gag aag acg gac cgc gtg gac gcg ctg cgg aag gcc gcc ggt    2087
Thr Trp Glu Lys Thr Asp Arg Val Asp Ala Leu Arg Lys Ala Ala Gly
                405                 410                 415 ctg gag agc tgatctcctg ccgcttgttc actgaggccg tgcccctcaa            2136
Leu Glu Ser
        420 ggggcaccgg gcctcagtgc gtcagctgct ggagccgttc ggcatcgaca cgtcgtcgcc    2196 ctcgtcgggg tcttgaggcc cgaagcgccg ccggatgtcg tcaacgacat cgggcttgtc    2256 gtgggcgtgg gcgagcttga tgagccgctc gacgaacagg tcgcgttccg gggcctcggg    2316 ggagatgccg aaccatttca ggaaggcgtc gac                                2349

<210> SEQ ID NO 2
<211> LENGTH: 420
<212> TYPE: PRT
<213> ORGANISM: Steptomyces spectabilis ATCC 27741

<400> SEQUENCE: 2

Met Ser Arg Arg Leu Phe Thr Ser Glu Ser Val Thr Glu Gly His Pro
1               5                   10                  15

Asp Lys Ile Ala Asp Gln Ile Ser Asp Thr Ile Leu Asp Ala Leu Leu
            20                  25                  30

Arg Glu Asp Pro Thr Ser Arg Val Ala Val Glu Thr Leu Ile Thr Thr
        35                  40                  45

Gly Leu Val His Val Ala Gly Glu Val Thr Thr Lys Ala Tyr Ala Pro
    50                  55                  60

Ile Ala Gln Leu Val Arg Glu Lys Ile Leu Glu Ile Gly Tyr Asp Ser
65                  70                  75                  80

Ser Lys Lys Gly Phe Asp Gly Ala Ser Cys Gly Val Ser Val Ser Ile
                85                  90                  95

Gly Ala Gln Ser Pro Asp Ile Ala Gln Gly Val Asp Thr Ala Tyr Glu
            100                 105                 110

Ser Arg Val Glu Gly Asp Glu Asp Glu Leu Asp Arg Gln Gly Ala Gly
        115                 120                 125

Asp Gln Gly Leu Met Phe Gly Tyr Ala Cys Asp Glu Thr Pro Glu Leu
    130                 135                 140

Met Pro Leu Pro Ile His Leu Ala His Arg Leu Ser Arg Arg Leu Ser
145                 150                 155                 160

Glu Val Arg Lys Asn Gly Thr Ile Pro Tyr Leu Arg Pro Asp Gly Lys
                165                 170                 175

Thr Gln Val Thr Ile Glu Tyr Asp Gly Asp Lys Ala Val Arg Leu Asp
            180                 185                 190
```

-continued

```
Thr Val Val Ser Ser Gln His Ala Ser Asp Ile Asp Leu Glu Ser
        195                 200                 205

Leu Leu Ala Pro Asp Ile Arg Glu Phe Val Val Glu Pro Glu Leu Lys
210                 215                 220

Ala Leu Val Glu Asp Gly Ile Lys Leu Val Glu Pro Glu Leu Lys
225                 230                 235                 240

Ala Leu Val Glu Asp Gly Ile Lys Leu Glu Thr Glu Gly Tyr Arg Leu
                245                 250                 255

Leu Val Asn Pro Thr Gly Arg Phe Glu Ile Gly Gly Pro Met Gly Asp
                260                 265                 270

Ala Gly Leu Thr Gly Arg Lys Ile Ile Ile Asp Thr Tyr Gly Gly Met
                275                 280                 285

Ser Arg His Gly Gly Gly Ala Phe Ser Gly Lys Asp Pro Ser Lys Val
                290                 295                 300

Asp Arg Ser Ala Ala Tyr Ala Met Arg Trp Val Ala Lys Asn Val Val
305                 310                 315                 320

Ala Ala Gly Leu Ala Ser Arg Cys Glu Val Gln Val Ala Tyr Ala Ile
                325                 330                 335

Gly Lys Ala Glu Pro Val Gly Leu Phe Val Glu Thr Phe Gly Thr Asn
                340                 345                 350

Thr Ile Asp Thr Asp Lys Ile Glu Gln Ala Ile Ser Glu Val Phe Asp
                355                 360                 365

Leu Arg Pro Ala Ala Ile Ile Arg Ser Leu Asp Leu Arg Pro Ile
                370                 375                 380

Tyr Ser Gln Thr Ala Ala Tyr Gly His Phe Gly Arg Ser Leu Pro Glu
385                 390                 395                 400

Phe Thr Trp Glu Lys Thr Asp Arg Val Asp Ala Leu Arg Lys Ala Ala
                405                 410                 415

Gly Leu Glu Ser
                420

<210> SEQ ID NO 3
<211> LENGTH: 423
<212> TYPE: PRT
<213> ORGANISM: Steptomyces spectabilis ATCC 27741

<400> SEQUENCE: 3

Met Ser Arg Arg Leu Phe Thr Ser Glu Ser Val Thr Glu Gly His Pro
1               5                   10                  15

Asp Lys Ile Ala Asp Gln Ile Ser Asp Thr Ile Leu Asp Ala Leu Leu
                20                  25                  30

Arg Glu Asp Pro Thr Ser Arg Val Ala Val Glu Thr Leu Ile Thr Thr
                35                  40                  45

Gly Leu Val His Val Ala Gly Glu Val Thr Thr Lys Ala Tyr Ala Pro
        50                  55                  60

Ile Ala Gln Leu Val Arg Glu Lys Ile Leu Lys Ile Glu Ile Gly
65                  70                  75                  80

Tyr Asp Ser Ser Lys Lys Gly Phe Asp Gly Ala Ser Cys Gly Val Ser
                85                  90                  95

Val Ser Ile Gly Ala Gln Ser Pro Asp Ile Ala Gln Gly Val Asp Thr
                100                 105                 110

Ala Tyr Glu Ser Arg Val Glu Gly Asp Glu Asp Glu Leu Asp Arg Gln
                115                 120                 125

Gly Ala Gly Asp Gln Gly Leu Met Phe Gly Tyr Ala Cys Asp Glu Tyr
                130                 135                 140
```

-continued

```
Pro Glu Leu Met Pro Leu Pro Ile His Leu Ala His Arg Leu Ser Arg
145                 150                 155                 160

Arg Leu Ser Glu Val Arg Lys Asn Gly Thr Ile Pro Tyr Leu Arg Pro
            165                 170                 175

Asp Gly Lys Thr Gln Val Thr Ile Glu Tyr Asp Gly Asp Lys Ala Val
            180                 185                 190

Arg Leu Asp Thr Val Val Val Ser Ser Gln His Ala Ser Asp Ile Asp
            195                 200                 205

Leu Glu Ser Leu Leu Ala Pro Asp Ile Arg Glu Phe Val Val Glu Pro
            210                 215                 220

Glu Leu Lys Ala Leu Val Glu Asp Gly Ile Lys Leu Val Val Glu Pro
225                 230                 235                 240

Glu Leu Lys Ala Leu Val Glu Asp Gly Ile Lys Leu Glu Thr Glu Gly
            245                 250                 255

Tyr Arg Leu Leu Val Asn Pro Thr Gly Arg Phe Glu Ile Gly Gly Pro
            260                 265                 270

Met Gly Asp Ala Gly Leu Thr Gly Arg Lys Ile Ile Ile Asp Thr Tyr
            275                 280                 285

Gly Gly Met Ser Arg His Gly Gly Gly Ala Phe Ser Gly Lys Asp Pro
            290                 295                 300

Ser Lys Val Asp Arg Ser Ala Ala Tyr Ala Met Arg Trp Val Ala Lys
305                 310                 315                 320

Asn Val Val Ala Ala Gly Leu Ala Ser Arg Cys Glu Val Gln Val Ala
            325                 330                 335

Tyr Ala Ile Gly Lys Ala Glu Pro Val Gly Leu Phe Val Glu Thr Phe
            340                 345                 350

Gly Tyr Asn Thr Ile Asp Thr Asp Lys Ile Glu Gln Ala Ile Ser Glu
            355                 360                 365

Val Phe Asp Leu Arg Pro Ala Ala Ile Ile Arg Ser Leu Asp Leu Leu
            370                 375                 380

Arg Pro Ile Tyr Ser Gln Thr Ala Ala Tyr Gly His Phe Gly Arg Ser
385                 390                 395                 400

Leu Pro Glu Phe Thr Trp Glu Lys Thr Asp Arg Val Asp Ala Leu Arg
            405                 410                 415

Lys Ala Ala Gly Leu Glu Ser
            420
```